US00PP33216P2

(12) United States Plant Patent
Van Swieten

(10) Patent No.: US PP33,216 P2
(45) Date of Patent: Jun. 29, 2021

(54) ***PHALAENOPSIS* ORCHID PLANT NAMED 'PHALJAKYJE'**

(50) Latin Name: ***Phalaenopsis* hybrid**
Varietal Denomination: PHALJAKYJE

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 16/974,383

(22) Filed: Jan. 6, 2021

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named, 'PHALJAKYJE', QZ PBR 2020/0289, filed Jan. 30, 2020.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALJAKYJE', particularly characterized by purplish-red flowers with dark red-purple lips, a slightly concave flower shape in lateral view, dark red-purple whiskers with white tips, and is propagated by meristem tissue culture, is disclosed.

3 Drawing Sheets

Genus and species: *Phalaenopsis* hybrid.
Variety denomination: 'PHALJAKYJE'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALJAKYJE'.

The new *Phalaenopsis* plant is a product of a planned breeding program conducted by the inventor in Bleiswijk, the Netherlands. The objective of this breeding program was to create a new *Phalaenopsis* plant with attractive, purplish-red flowers with dark red-purple lips, suitable for potted plant production.

The new *Phalaenopsis* plant 'PHALJAKYJE' is a result of cross-pollination made by the inventor in May 2013 in Bleiswijk, the Netherlands, of the proprietary female, or seed parent, *Phalaenopsis* hybrid '01-4320' (unpatented) with the proprietary male, or pollen parent, *Phalaenopsis* hybrid '41754-06' (unpatented).

The new *Phalaenopsis* was selected by the inventor as a single plant within the progeny of the stated cross-pollination in a controlled greenhouse in Bleiswijk, the Netherlands, in April 2016.Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 30, 2020 (Application no. 2020/0289), by Applicant who obtained the subject matter disclosed directly from the inventor. 'PHALJAKYJE' has not been made publicly available or sold anywhere in the world prior to the effective filing date of this application with the exception of sales or disclosures made one year or less before the effective filing date of this claimed invention by Applicant who obtained 'PHALJAKYJE' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALJAKYJE' as a new and distinct variety of *Phalaenopsis* plant:

1) Purplish-red flowers with dark red-purple lips;
2) Flower shape in lateral view is slightly concave; and
3) Dark red-purple whiskers with white tips.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs were taken in a greenhouse in Bleiswijk, the Netherlands, from 50-week-old plants in November 2020. Colors in the photographs may differ from the color values cited in the detailed botanical description, which accurately describe the actual colors of the new variety.

DESCRIPTION OF THE NEW VARIETY

Figure 1:
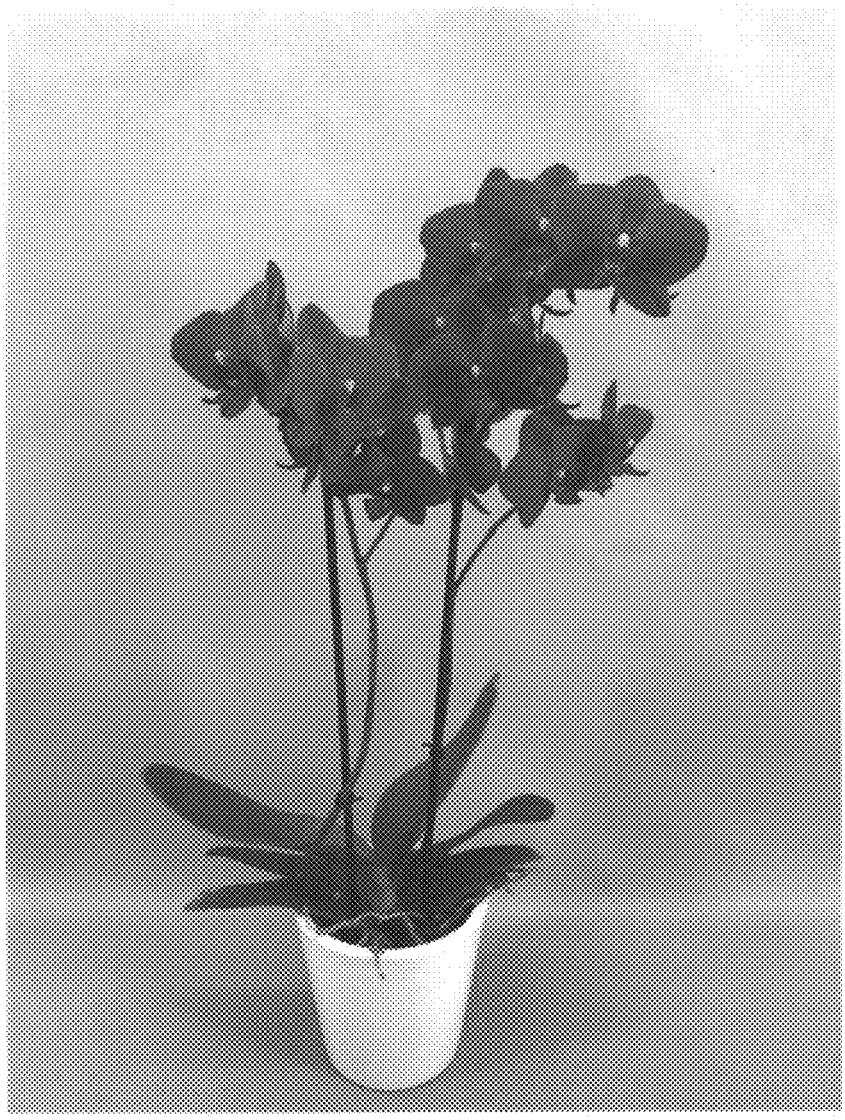
FIG. 1 shows the overall plant habit, including blooms and foliage of 'PHALJAKYJE'.
Figure 2:
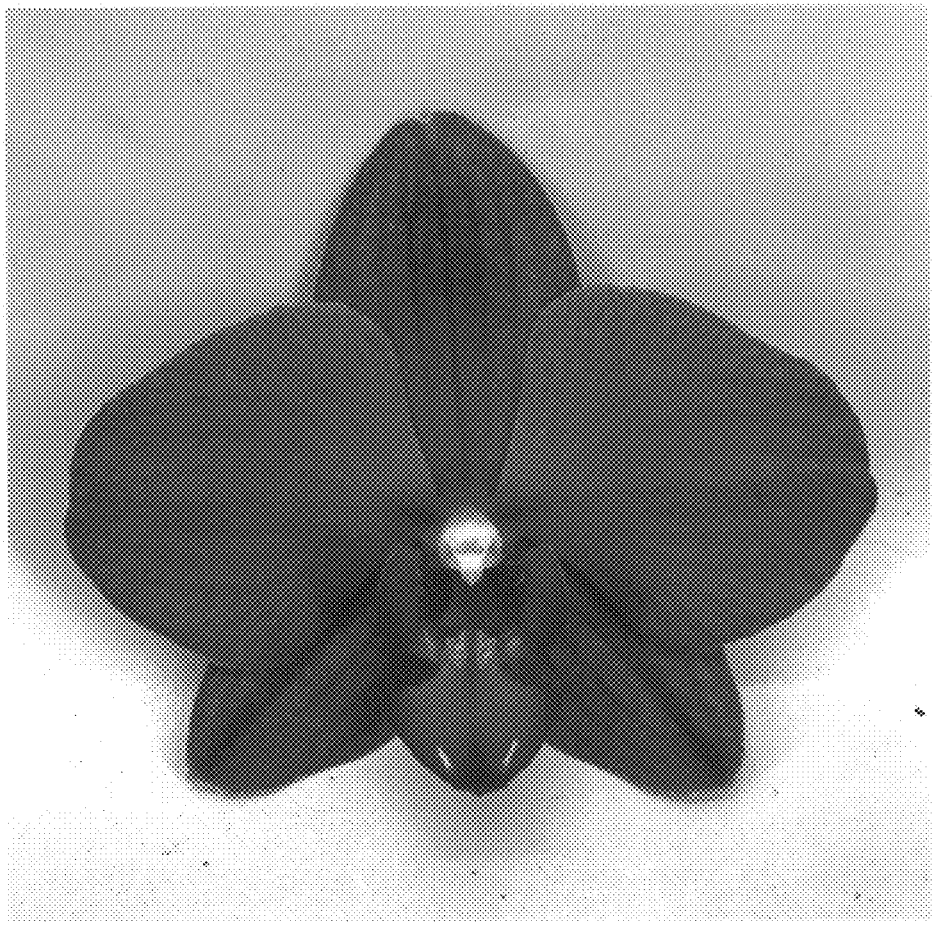
FIG. 2 shows a close-up of a flower of 'PHALJAKYJE'.
Figure 3:
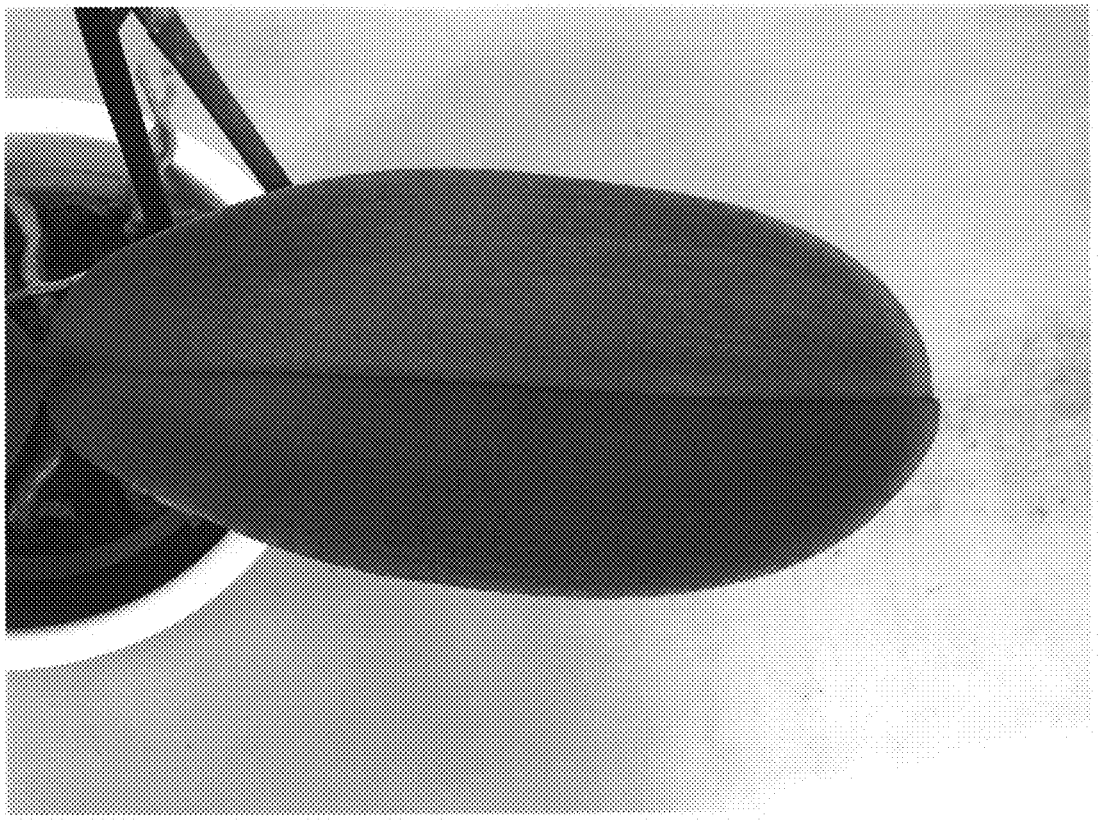
FIG. 3 shows an overhead view of the leaves of 'PHALJAKYJE'.

The following detailed description sets forth the distinctive characteristics of 'PHALJAKYJE'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in November 2020 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALJAKYJE'.

Parentage:

*Female parent*.—*Phalaenopsis* cultivar '01-4320' (unpatented).

*Male parent*.—*Phalaenopsis* cultivar '41754-06' (unpatented).

Propagation:

*Type*.—Meristem tissue culture.

Roots:

*Root description*.—Greyed-green (something between RHS 190B and 190C) colored roots with branching lateral roots having yellow-green (something in between RHS 144C and N144C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with panicle inflorescence.

*Height (from soil level to top of inflorescence)*.—Approximately 53.0 cm to 58.0 cm.

*Width (measured from leaf tips)*.—About 29.0 cm to 31.0 cm.

*Vigor*.—Strong.

Leaves:

*Mature leaves*.—Quantity per plant: 7 to 9 leaves are produced before flowering. Length (fully expanded): 17.0 cm to 20.0 cm. Width: 8.5 cm to 9.5 cm. Position of the broadest part of the leaf: At the middle. Shape: Oblong. Base shape: Moderately elongated. Apex: Obtuse, slightly asymmetric. Leaf blade angle with the petiole (measured from the horizontal position): Between 25 degrees and 40 degrees. Leaf margin: Entire. Color: Upper surface: RHS 146A. Lower surface: RHS 146B. Texture (both upper and lower surfaces): Smooth. Thickness: 2.2 mm to 2.5 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—11 to 19.

*Length*.—53.0 cm to 58.0 cm.

*Diameter*.—5.0 mm to 6.0 mm.

*Strength*.—Strong.

*Aspect*.—Upright to slightly pendent.

*Texture*.—Smooth.

*Color*.—Green (RHS 146B) with a touch of brown (RHS N199A).

*Internode length*.—3.0 cm to 5.0 cm.

Inflorescence description:

*Appearance*.—Upright to slightly pendent, panicle inflorescence with bilaterally symmetrical flowers that open in succession beginning with the lowermost flower.

*Number of inflorescences:* 1 to 2.

*Inflorescence size*.—Height (from base to tip): 240.0 mm to 310.0 mm.

*Flowering time*.—First flowers can be expected 10 to 11 months after planting in a 12-cm pot.

*Flower*.—Height: 70.0 mm to 75.0 mm. Diameter: 75.0 mm to 80.0 mm. Depth of lip: 22.0 mm to 24.0 mm.

*Flower longevity*.—On the plant: 8 to 10 weeks.

*Flower shape*.—Slightly concave.

*Fragrance*.—Absent.

*Flower bud*.—Average size: Medium. Length: 19.0 mm to 21.0 mm. Width: 14.0 mm to 16.0 mm. Shape: Egg shaped. Color: Yellow-green (RHS 146C) with dark purplish-red shade and stripes (something in between RHS N79B and N79C).

*Petals*.—Arrangement: Open/free. Shape: Semi-circular. Apex: Rounded to slightly emarginated asymmetric. Margin: Weakly undulated. Length (from base to tip): 35.0 mm to 37.0 mm. Width: 38.0 mm to 40.0 mm. Position of the broadest part of the petal: Toward the base. Color (when fully opened): Upper surface: Basic color: Purplish-red (RHS 59B). Over color: Purplish-red (RHS 64A) toward margin; stripes (RHS 59A). Lower surface: Basic color: Purplish-red (RHS 186A). Over color: Light yellow-green (RHS 145C) at the middle. Number of spots and stripes on the petals (upper surface): Many stripes. Color of spots and stripes on the petals (upper surface): RHS 59A. Density of netting of the petals (upper surface): None. Color of the netting (upper surface): None.

*Dorsal sepal*.—Shape: Elliptic. Apex: Emarginated symmetric. Margin: Entire. Length (from base to tip): 40.0 mm to 42.0 mm. Width: 29.0 mm to 31.0 mm. Position of the broadest part of the dorsal sepals: Toward the base. Color (when fully opened): Upper surface: Basic color: Purplish-red (RHS 59B). Over color: Dark red stripes (RHS 59A). Lower surface: Basic color: Dark purplish-red (RHS N79C) on sides toward margin. Over color: Light yellow-green (RHS 145C) in the middle. Number of spots and stripes on the dorsal sepals (upper surface): Medium to many stripes. Color of spots and stripes on the dorsal sepals (upper surface): RHS 59A. Density of netting of the dorsal sepals (upper surface): Low. Color of the netting: RHS 59A.

*Lateral sepals*.—Shape: Ovate. Apex: Obtuse asymmetric. Margin: Entire. Length (from base to tip): 39.0 mm to 41.0 mm. Width: 27.0 mm to 29.0 mm. Position of the broadest part of the lateral sepals: Toward the base. Color (when fully opened): Upper surface: Basic color: Purplish-red (RHS 59B). Over color: Hint of light yellow-green (RHS 145C); spotted (RHS 59A) at the base; stripes (RHS 59A). Lower surface: Basic color: Dark purplish-red (RHS N79C) on sides toward margin. Over color: Light yellow-green (RHS 145C) at the middle from base toward the apex; dark red stripes (RHS 187C). Number of spots and stripes on the lateral sepals (upper surface): Medium stripes and few spots at the base. Color of spots and stripes on the lateral sepals (upper surface): Stripes and spots (RHS 59A). Density of netting of the lateral sepals (upper surface): Medium. Color of the netting (upper surface): RHS 59A.

*Labellum* (*lip*).—Whiskers: Present. Length of whiskers: 5.0 mm to 7.0 mm. Color of whiskers: Dark red-purple (something in between RHS 59A and 59B) at the base with white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Undulated (widely wavy). Length: 14.0 mm to 16.0 mm. Width: 7.0 mm to 9.0 mm. Color: Upper surface: Hint of yellow (RHS 12A) with stripes (RHS 187B) at the base; dark red (RHS 187B) and dark purplish-red (RHS N79C) toward the tip. Lower surface: Yellowish-white (RHS 156D) at the base toward one side and red (RHS 185A) toward the other side; dark reddish-purple (something in between RHS N78A and N79C) toward the tip. Number of spots and stripes on the lateral lobe: Few stripes. Color of spots and stripes on the lateral lobe: RHS 187B. Density of netting of the lateral lobe: None. Color of the netting: None.

*Apical lobe*.—Shape: Trullate. Margin: Entire. Length: 19.0 mm to 21.0 mm. Width: 17.0 mm to 19.0 mm. Color: Upper surface: Dark red-purple (something in between RHS 59A and 59B) at the base; reddish-purple (something in between RHS N78A and N79C) with a dark red middle stripe (RHS 187B) toward whiskers. Lower surface: Light greenish-yellow (RHS 160C) at the middle from base; red wings (RHS 184A); reddish-purple (something in between RHS N78A and N79C) with a white spot (RHS NN155C) at the middle toward whiskers. Number of spots and stripes on the apical lobe: None. Color of spots and stripes on the apical lobe: Not applicable. Density of netting of the apical lobe: None. Color of the netting: Not applicable.

*Callus*.—Average size: Small. Height: 4.0 mm to 5.0 mm. Length: 4.0 mm to 5.0 mm. Width: 3.0 mm to 4.0 mm. Color: Yellow (RHS 13A); spotted (RHS 59A).

Reproductive organs:

*Column*.—Length: 8.0 mm to 10.0 mm. Diameter: 5.0 mm to 6.0 mm. Color: Reddish-purple (RHS NN78A) at the base with lighter reddish-purple tip (RHS N78B).

*Pollinia*.—Quantity: 2. Diameter: 0.5 mm to 0.7 mm. Color: Orange-yellow (RHS 23A).

*Ovary*.—Length: 9.0 mm to 11.0 mm. Diameter: 2.6 mm to 2.8 mm.

*Pedicel*.—Length: 32.0 mm to 34.0 mm. Diameter: 2.9 mm to 3.1 mm. Texture: Smooth. Color: Hint of yellow-green (RHS 146C) at the base; light yellow-green (RHS 145C) at the middle and very light purple (RHS 76C) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALJAKYJE' differs from the female parent plant '01-4320' (unpatented), in that 'PHALJAKYJE' has weakly spatulate lateral lobes, whereas '01-4320' has spatulate lateral lobes. Additionally, 'PHALJAKYJE' has smaller flowers than '01-4320'.

'PHALJAKYJE' differs from the male parent plant '41754-06' (unpatented) in that 'PHALJAKYJE' has weakly spatulate lateral lobes and has whiskers, whereas '41754-06' has ligulate lateral lobes and does not have whiskers. Additionally, 'PHALJAKYJE' has larger flowers than '41754-06'.

'PHALJAKYJE' is most similar to the commercial *Phalaenopsis* plants named 'PHALVILMYK' (U.S. Plant Pat. No. 32,008) and 'PHALAPEK' (unpatented). 'PHALJAKYJE' differs from the commercial variety 'PHALVILMYK' in that 'PHALJAKYJE' has trullate apical lobes and purplish-red flowers, whereas 'PHALVILMYK' has rhombic apical lobes and red flowers. Additionally, 'PHALJAKYJE' has longer leaves than 'PHALVILMYK'.

'PHALJAKYJE' differs from the commercial variety 'PHALAPEK' in that 'PHALJAKYJE' has trullate apical lobes, dark red-purple whiskers with white tips, and panicle inflorescence, whereas 'PHALAPEK' has rhombic apical lobes, dark red whiskers, and raceme inflorescence.

I claim:

1. A new and distinct variety of *Phalaenopsis* plant named 'PHALJAKYJE', substantially as described and illustrated herein.

* * * * *